(12) United States Patent
Cahilly

(10) Patent No.: US 10,677,694 B1
(45) Date of Patent: Jun. 9, 2020

(54) SAMPLE MANIPULATION APPARATUS

(71) Applicant: Bambi Lyn Cahilly, Las Vegas, NV (US)

(72) Inventor: Bambi Lyn Cahilly, Las Vegas, NV (US)

(*) Notice: Subject to any disclaimer, the term of this patent is extended or adjusted under 35 U.S.C. 154(b) by 0 days.

(21) Appl. No.: 16/287,532

(22) Filed: Feb. 27, 2019

(51) Int. Cl.
| | |
|---|---|
| *G01N 1/38* | (2006.01) |
| *B01L 3/00* | (2006.01) |
| *B01L 3/06* | (2006.01) |
| *G01N 1/28* | (2006.01) |
| *B01L 3/18* | (2006.01) |
| *C12M 1/26* | (2006.01) |
| *C12M 1/30* | (2006.01) |

(52) U.S. Cl.
CPC ............... *G01N 1/38* (2013.01); *B01L 3/06* (2013.01); *B01L 3/508* (2013.01); *G01N 1/2813* (2013.01); *B01L 3/18* (2013.01); *C12M 33/00* (2013.01); *C12M 33/02* (2013.01)

(58) Field of Classification Search
CPC ............ B01L 3/188; B01L 3/508; B01L 3/06; C12M 33/00; C12M 33/02; G01N 1/38; G01N 1/2813
USPC ....... 73/864, 864.41; D24/133, 216; 435/30, 435/309.1, 309.3
See application file for complete search history.

(56) References Cited

U.S. PATENT DOCUMENTS

| | | | | |
|---|---|---|---|---|
| 3,875,015 | A | * | 4/1975 | Wadley .................. C12M 33/02 435/30 |
| D282,278 | S | * | 1/1986 | Asa .............................. D24/133 |
| 8,709,362 | B2 | * | 4/2014 | Leventhal ................. B01L 3/18 422/547 |
| 2008/0011107 | A1 | * | 1/2008 | Leventhal ................. B01L 3/18 73/864 |
| 2010/0178698 | A1 | * | 7/2010 | Becker ................... C12M 23/10 435/348 |
| 2012/0297902 | A1 | * | 11/2012 | Leventhal ................. B01L 3/18 73/864 |
| 2012/0315702 | A1 | * | 12/2012 | Chesnut ................. C12M 33/18 435/379 |
| 2013/0205922 | A1 | * | 8/2013 | Leventhal ................. B01L 3/18 73/864.01 |
| 2014/0230578 | A1 | * | 8/2014 | Leventhal ................. B01L 3/18 73/864 |

FOREIGN PATENT DOCUMENTS

| | | | | |
|---|---|---|---|---|
| GB | 2391017 | A | * 1/2004 | .............. C12M 1/26 |
| WO | WO-8808024 | A1 | * 10/1988 | ............ C12M 23/10 |

* cited by examiner

*Primary Examiner* — Jonathan M Dunlap
(74) *Attorney, Agent, or Firm* — Theodore J. Bielen, Jr.

(57) ABSTRACT

A container sample manipulation apparatus utilizing a handle with a terminal portion. The apparatus may be manually operated in an upright position or in a tilted configuration in conjunction with a guide for interaction with the structure of a sample container.

14 Claims, 5 Drawing Sheets

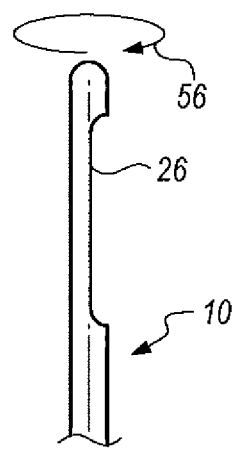
FIG. 7
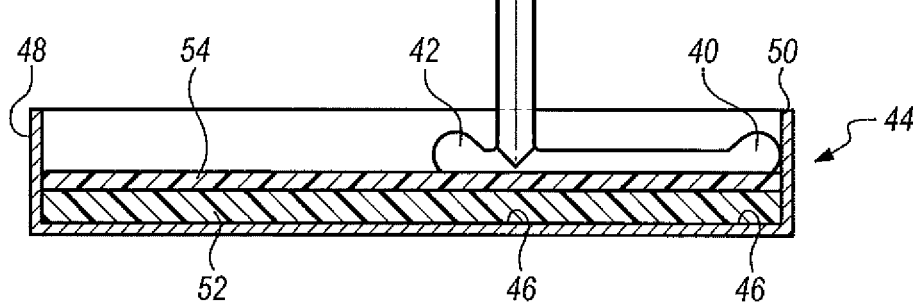
FIG. 8
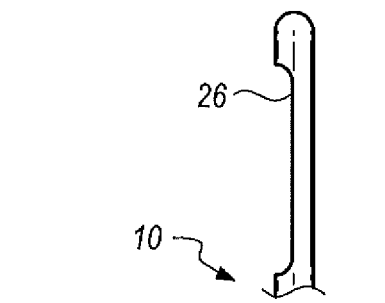
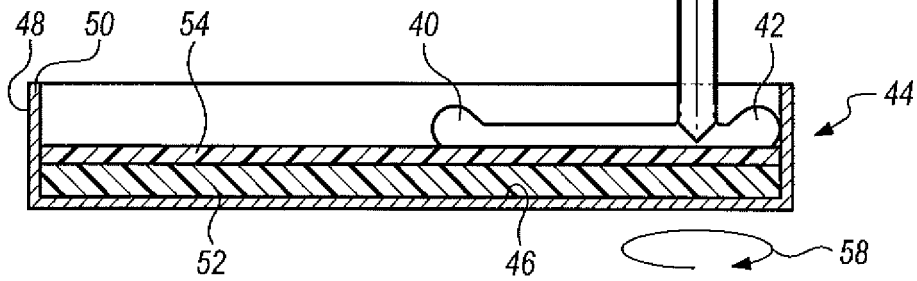

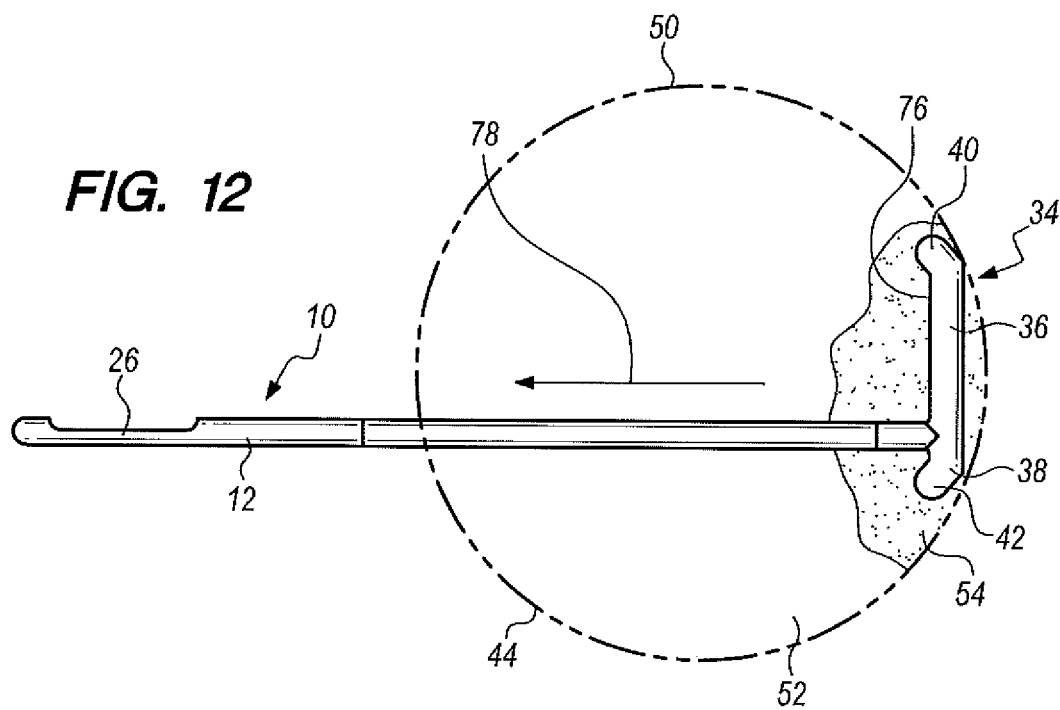
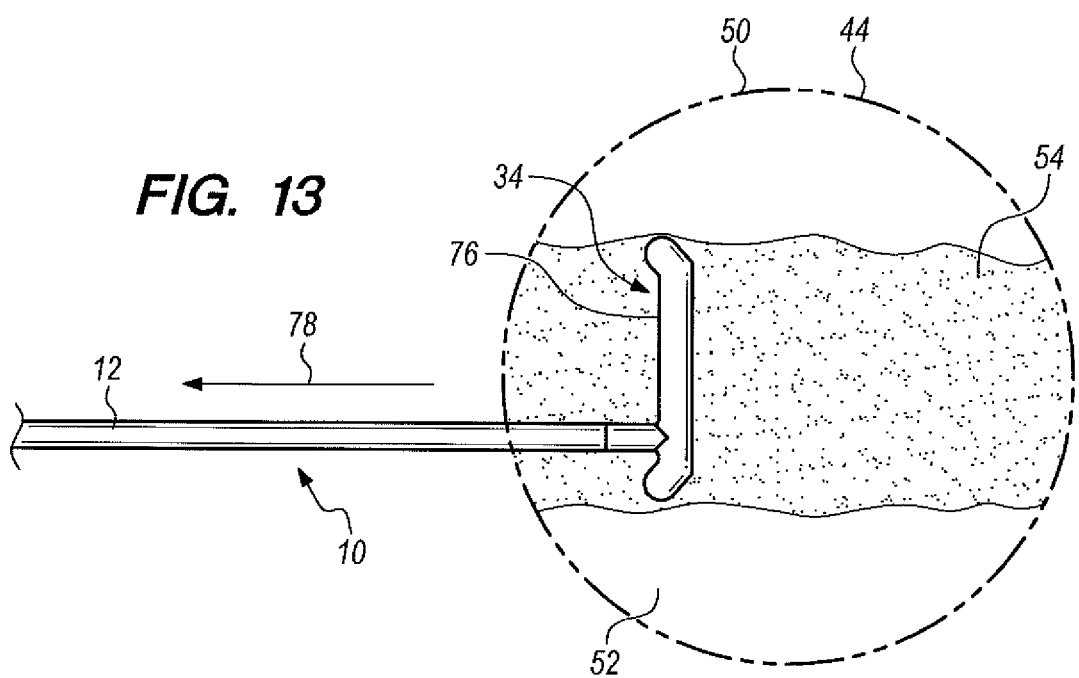

SAMPLE MANIPULATION APPARATUS

BACKGROUND OF THE INVENTION

The present application relates to a novel and useful sample manipulation apparatus which is especially useful in the field of scientific research.

Petri dishes are commonly used by biologists and other scientists to culture cells, observe plant germination, and the like. Also, petri dishes are simply used to dry fluids in an oven and to carry and store samples of all types.

Once a petri dish is plated with an agar, a sample to be studied is placed thereupon. Such sample must be dispersed or spread atop the agar in order to properly study such sample during scientific tests.

In the past, stirring rods and the like have been used to stir or manipulate the samples. However, such stirrers of the prior art are limited in function and are not able to conveniently and efficiently mix and spread such samples on the agar base.

A sample manipulation device which is capable of spreading or dispersing samples on an agar using multiple manual techniques would be a notable advance in the laboratory arts.

SUMMARY OF THE INVENTION

In accordance with the present application, a novel and useful sample manipulation apparatus is herein provided.

The apparatus of the present application may be manually operated with a container having a base with an extending wall portion having an end rim. Such container may take the form of a petri dish. The tool of the present application employs a handle having an outer surface. The handle includes a first flattened surface portion on the outer surface facing in a first direction. A second flattened surface portion of the outer surface of the handle is also found in the present apparatus and faces a second direction. The first flattened surface portion of the outer surface of the handle takes the form of a guide to allow sliding engagement of the handle with the rim of the container and to resist rotation of the handle during this maneuver.

A terminal member is also found in the apparatus of the present application. The terminal member includes a first leg and a second leg each having an elongated dimension. The elongated dimension of the first leg extends a greater distance than the elongated dimension of the second leg. Such first and second legs are connected to the handle.

A first tip is also employed in the apparatus of the present application and connects to and angularly extends from the first leg. A second tip connects to and angularly extends from the second leg. The first leg, second leg, first tip, and second tip form a concave pocket that is movable along the base of the container with the sliding motion of the handle at the rim of the container, above described.

In certain instances, the handle is formed with at least a portion thereof in the form of a cylindrical cross-sectional member. Also, the first and second legs of the terminal member may comprise an ovate cross-sectional configuration. Likewise, the first and second tips of the first and second legs of the terminal member may possess a rounded end surface.

The handle may also be fashioned such that a rounded intermediate portion lies between the first and second flattened surface portions. In this manner, the second flattened surfaces portion serves as a grip to allow the pushing and pulling of the handle while the first flattened portion slidingly engages the rim of the container. Likewise, the rounded portion between the first and second flattened surface portions of the handle would allow the user to manually impart a spinning motion to the apparatus of the present application in order to permit the terminal member to sweep the sample above the surface of the base of the container. The latter maneuver is accomplished when the handle is in an upright position and the user is preferably gripping the rounded intermediate portion of the handle.

It may be apparent that a novel and useful sample manipulation apparatus has been hereinabove described.

It is therefore an object of the present application to provide a sample manipulation apparatus that may be cooperatively used with a petri dish to position or spread sample therewithin.

Another object of the present application is to provide a sample manipulation apparatus that readily imparts a raking or sweeping motion to a sample located within a container.

Another object of the present application is to provide a sample manipulation apparatus that aids in the prevention of contamination of a sample found in a container used in a scientific analysis.

Another object of the present application is to provide a sample manipulation apparatus that may be held in an upright position or a tilted position to apply different forces on a sample within a petri dish.

Another object of the present application is to provide a sample manipulation apparatus that is capable of spreading a sample in a petri dish and avoids pooling of the sample along the wall portion thereof.

Another object of the present application is to provide a sample manipulation apparatus that is stable or balanced when used to spread a sample in a petri dish.

Another object of the present application is to provide a sample manipulation apparatus that is easily sterilized and is compatible with like samples in a petri dish.

The apparatus of the present application possesses other objects and advantages especially as concerns particular characteristics and features thereof which will become apparent as the specification continues.

BRIEF DESCRIPTION OF THE SEVERAL VIEWS OF THE DRAWINGS

FIG. 7 is a side elevational view of the apparatus of the present application in its upright spinning orientation with respect to a petri dish.

FIG. 8 is a side elevational view of the apparatus of the present application in an upright position in a sample container during rotation of the sample container.

FIG. 12 is a top plan view of the apparatus of the present application used in conjunction with a petri dish depicted schematically.

FIG. 13 is a top plan view of the apparatus of the present application used in conjunction with a petri dish depicted schematically and indicating the raking movement of the apparatus relative to a sample in a petri dish.

For a better understanding of the application, reference is made to the following detailed description of the preferred embodiments thereof which should be referenced to the prior described drawings.

DETAILED DESCRIPTION OF THE PREFERRED EMBODIMENTS

Various aspects of the present application will evolve from the following detailed description of the preferred embodiments thereof which should be referenced to the prior delineated drawings.

Figure 1:
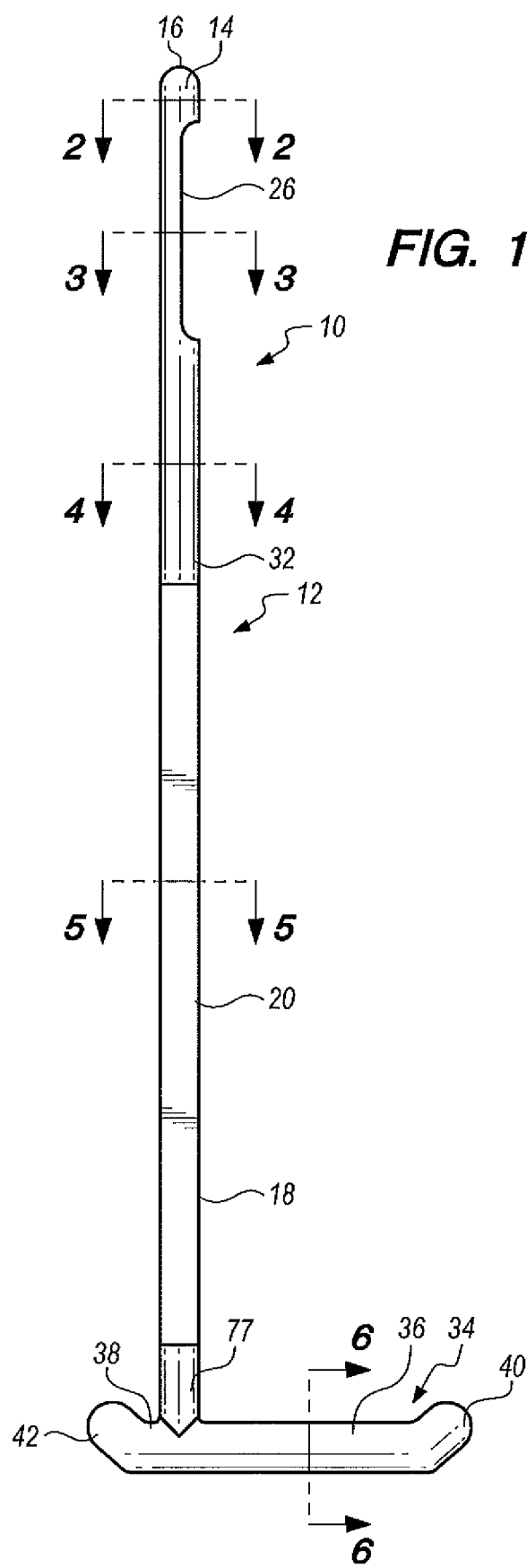
FIG. 1 is a side elevational view of the apparatus of the present application.
Figure 2:
FIG. 2 is a sectional view taken along line 2-2 of FIG. 1.
Figure 5:
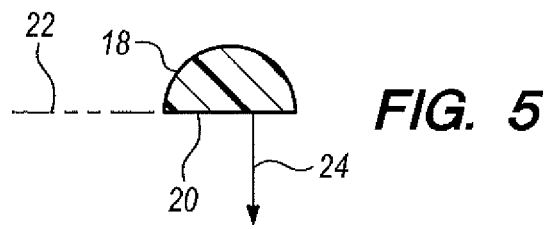
FIG. 5 is a sectional view taken along line 5-5 of FIG. 1.

With reference to FIG. 1, it may be observed that the apparatus of the present application is shown as a whole and denoted by reference character 10. Apparatus 10 is intended for use as a sample manipulation tool in conjunction with containers used in scientific analyses, which will be discussed in detail as the specification continues. Apparatus 10 includes a handle 12. Handle 12 is generally cylindrical in cross-sectional configuration and possesses a rounded section 14 at end 16 thereof. Handle 14 also has an outer surface 18 and a first flattened surface portion 20. Flattened surface portion 20 may lie along a plane 22 such that first flattened surface portion 20 faces in a direction indicated by directional arrow 24, FIG. 5.

Figure 3:
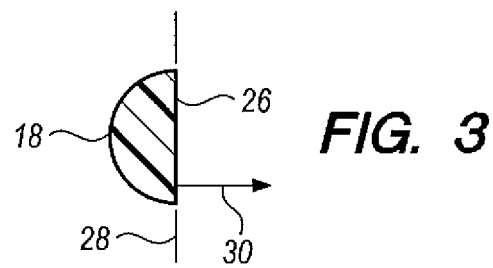
FIG. 3 is a sectional view taken along line 3-3 of FIG. 1.
Figure 4:
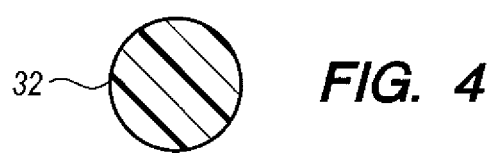
FIG. 4 is a sectional view taken along line 4-4 of FIG. 1.

Handle is further constructed with a second flattened surface portion 26 which may lie along a plane 28. Second flattened surface portion 26, thus, faces in a different direction than first flattened surface portion 20, as is indicated by directional arrow 30, FIG. 3. First and second flattened surfaces may serve as grips or control surfaces contacted by the fingers of a user, as is described hereinafter. Handle 12 further possesses an intermediate rounded portion 32 which lies between first flattened surface portion 20 and second flattened surface portion 26, FIG. 4.

Figure 6:
FIG. 6 is a sectional view taken along line 6-6 of FIG. 1.

The apparatus 10 of the present application is also formed with a terminal member 34 that is connected to handle 12. Terminal member 34 is fashioned with a first leg 36 and a second leg 38. As is shown in FIG. 6, first and second legs 36 and 38 may have an ovate cross-sectional configuration. In addition, a rounded tip 40 connects to and angularly extends from first leg 36, while a second rounded tip 42 connects to and angularly extends from second leg 38.

Figure 10:
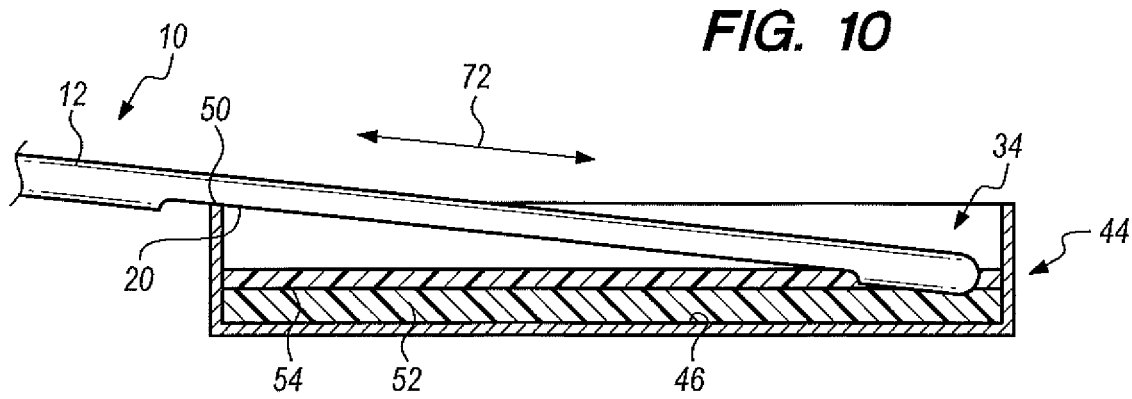
FIG. 10 is a partial side view of the apparatus of the present application within a petri dish depicted in phantom and illustrating the function of the guide element of the apparatus.

Apparatus 10 of the present application is ideally suited for use with a petri dish 44 depicted in section in FIGS. 7 and 8. Petri dish 44 is formed with a base 46 and a wall portion 48 having a rim 50 at the end of wall portion 48. As shown in FIGS. 7 and 8, petri dish 44 has been filled with an agar 52 below a sample 54, which is intended to be spread by apparatus 10. FIG. 10 shows the upright positioning of apparatus 10 in petri dish 44 and permits the manual turning or spinning of the same to spread sample 54 above agar 52, indicated by directional arrow 56. The user grips intermediate portion 32 of handle 12 to spin apparatus 10. FIG. 8 shows another upright orientation of apparatus 10 in which petri dish 44 is manually spun or turned by the hand of the user according to directional arrow 58 while apparatus 10 is held in a stationary position by the hand of the user, as shown. The user stabilizes apparatus 10 during this procedure by finger gripping apparatus 10 at flattened portions 20 and/or 26 of handle 12. In this manner, contamination of sample 54 is minimized since the user's hand lies generally away from sample 54. In addition, upturned tips 40 and 42 prevent the forcing and pooling of sample 54 between agar 52 and wall 48 of petri dish 44.

Figure 9:
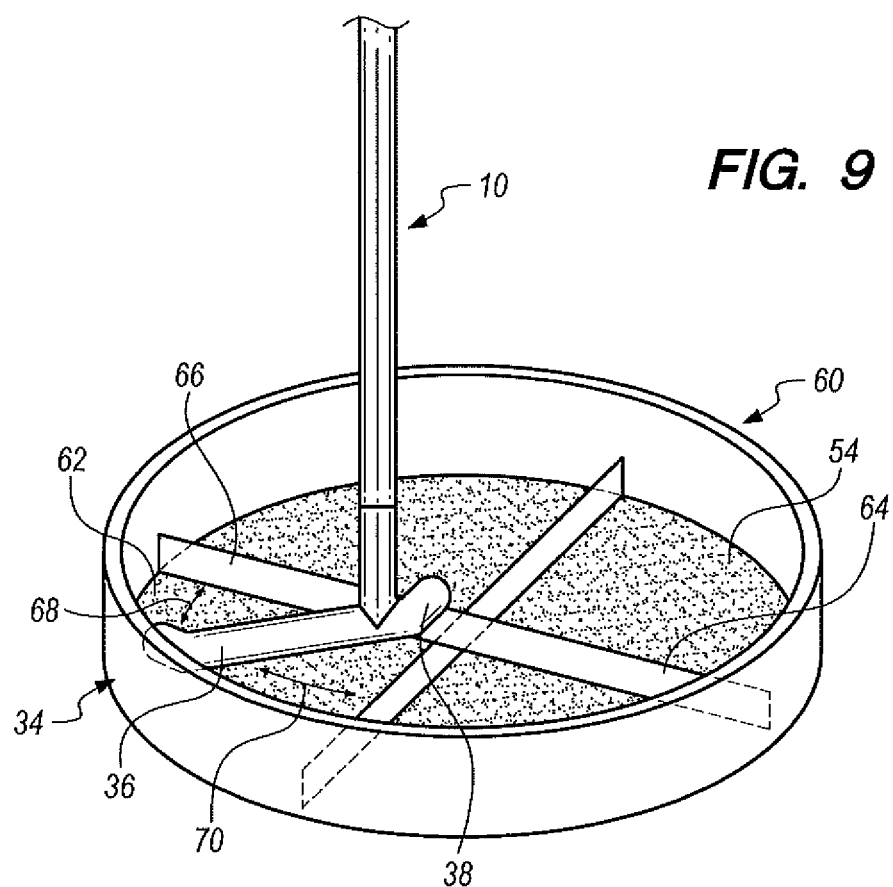
FIG. 9 is a top, front, right side perspective view of the device of the present application within a quadrant petri dish.

With reference to FIG. 9, a quadrant petri dish 60 is depicted. Apparatus 10 has been located within a sector 62 such that second leg 38 thereof lies at the conflux of dividers 64 and 66. In such an orientation, apparatus 10 is then swung back and forth within sector 62 to spread sample 54, generally through the swinging motion of first leg 36 of terminal member 34. Such swinging motion is indicated by directional arrows 68 and 70, FIG. 9. It should be realized that apparatus 10 may be employed with petri dishes having two or three sectors, also.

FIG. 10 illustrates the versatility of apparatus 10, where apparatus 10 has been tilted such that first flattened outer surface portion 20 serves as a guide to allow the sliding of handle 12 of apparatus 10 along rim 50 of petri dish 44 without the rotation of handle 12 in this position. Apparatus 10 is then moved along and through sample 54, as shown by directional arrow 72, in a raking motion. Sample 54 is subsequently spread above agar 52 by this motion and through the contact of terminus 34 with sample 54. Again, flattened surface portion 26 may be used as a control surface by the fingers of the user during this process.

Figure 11:
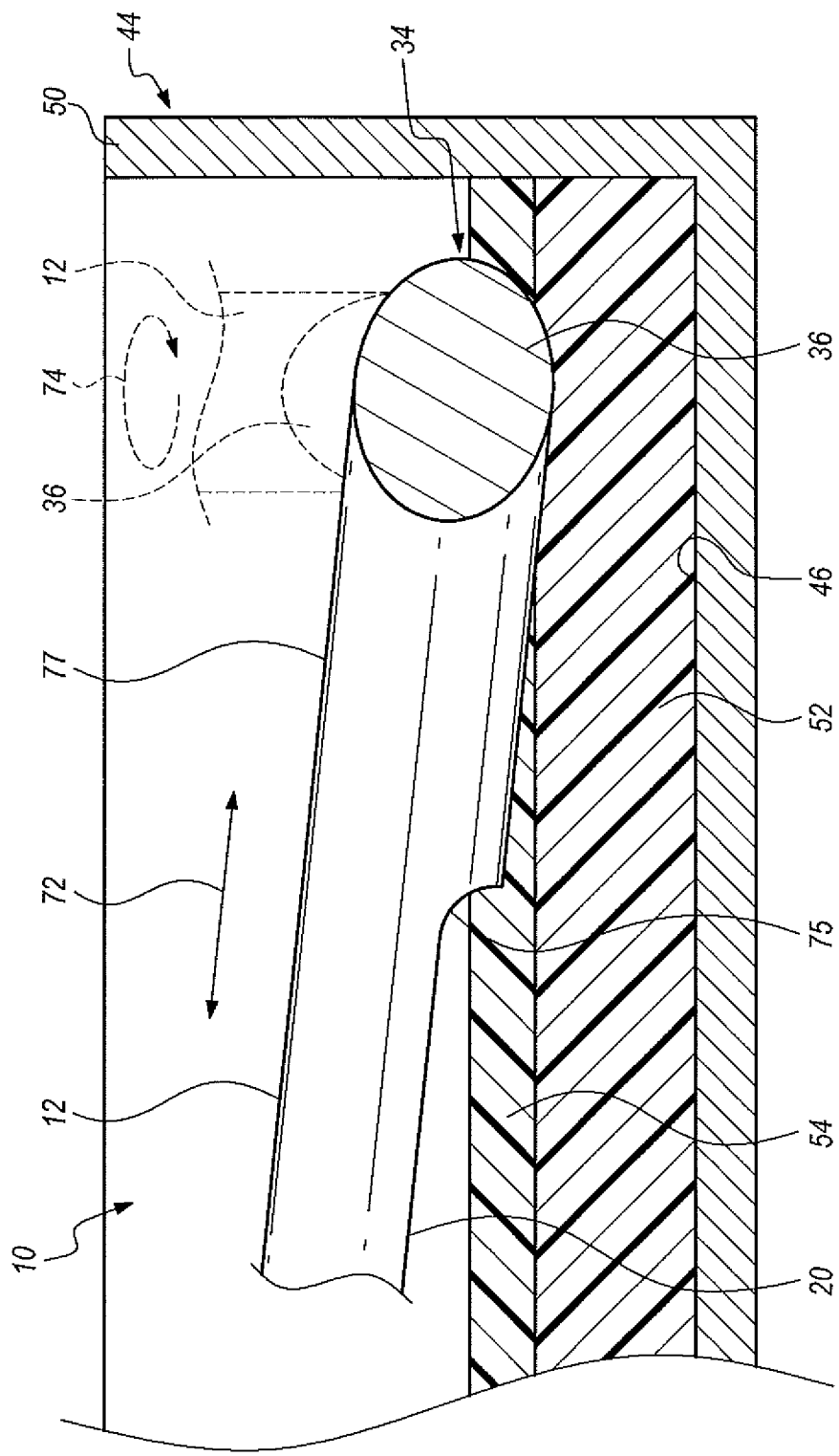
FIG. 11 is an enlarged partial side view of the apparatus of the present application with the terminus thereof shown in section and a container also depicted in section.

FIG. 11 shows the particulars of such raking function in which the ovate cross-sectional configuration of legs 36 and 38 ensures the thorough contact of legs 36 and 38 with sample 54 during the above described raking motion. FIG. 11 also illustrates the contact of terminus 34 with sample 54 when handle portion of apparatus 10 is in an upright position. The spinning or turning of apparatus 10 in such position is indicated by directional arrow 74.

A smooth transition area 75 is located between first flattened surface portion 20 and rounded portion 77, FIG. 11. Smooth transition area 75 prevents the tearing of a user's gloves when handle 12 is held at this area. Smooth transition area 75 also serves as a stop for a sample being distributed when apparatus 10 is in an upright position, as shown in FIGS. 7 and 8.

FIGS. 12 and 13 further demonstrate the raking function of apparatus 10 and depicts the open concave pocket 76 formed by first leg 36, second leg 38, tip 40, and tip 42 of terminal member 34. As may be seen, apparatus 10 has been moved to the left across sample 54 to spread the same when viewing FIGS. 12 and 13 sequentially. Directional arrow 78 reveals the pulling motion imparted to apparatus 10. Second flattened outer surface portion 26 may be employed to accommodate a finger, preferably a thumb, of the user when operating apparatus 10 in a raking format.

In operation, the user grasps apparatus 10 and positions the same either in an upright position, as illustrated in FIGS. 7 and 8, or in a tilted position, as shown in FIGS. 10-13. The former upright position is used to spin or turn apparatus 10 or to turn petri dish 44 relative to a stationary apparatus, resulting in the spreading of sample 54 above agar 52 within petri dish 44. The latter tilted position permits the user to rake sample 54 across agar 52 using first flattened outer surface portion 20 as a guide in combination with rim 50 of petri dish 44. First and second flattened surface portions 20 and 26 of handle 12 may be used as grips or control surfaces to accommodate the fingers of a user during these maneuvers.

While in the foregoing embodiments of the application have been set forth in considerable detail for the purposes of making a complete disclosure of the invention, it may be apparent to those of skill in the art that numerous changes may be made in such detail without departing from the spirit and principles of the application.

What is claimed is:

1. A sample manipulation apparatus, comprising:
a handle, said handle comprising an outer surface, said handle further comprising a first flattened surface portion of said outer surface, said first flattened surface portion facing in a first direction, and a second flattened surface portion of said outer surface, said second flattened surface portion facing in a second direction;
a terminal member, said terminal member comprising a first leg having an elongated dimension, and a second leg having an elongated dimension, said elongated dimension of said first leg being greater than said elongated dimension of said second leg, said first and second legs being connected to said handle;
a first tip connected to and angularly extending from said first leg;
a second tip connected to and angularly extending from said second leg; and
said first leg, second leg, first tip, and second tip forming a concave pocket.

2. The apparatus of claim 1 in which at least a portion of said handle comprises a cylindrical cross-sectional configuration.

3. The apparatus of claim 2 in which said first and second legs comprise an ovate cross-sectional configuration.

4. The apparatus of claim 3 in which said first and second tips each comprise a rounded outer surface.

5. The apparatus of claim 1 in which said handle further comprises a rounded intermediate portion lying between said first and second flattened surface portions of said outer surface of said handle.

6. The apparatus of claim 1 in which said first flattened outer surface portion of said handle lies in a first plane and said second flattened outer surface portion of said handle lies in a second plane, said first plane positioned in an intersecting relationship with said second plane.

7. The apparatus of claim 6 in which at least a portion of said handle comprises a cylindrical cross-sectional configuration.

8. The apparatus of claim 7 in which said first and second legs comprise an ovate cross-sectional configuration.

9. The apparatus of claim 8 in which said first and second tips each comprise a rounded outer surface.

10. The apparatus of claim 9 in which said handle further comprises a rounded intermediate portion lying between said first and second flattened surface portions.

11. The apparatus of claim 6 in which said first plane orthogonally intersects said second plane.

12. A sample manipulation apparatus used in configuration with a container having a base, and a wall extending therefrom, the wall of the container possessing a rim, comprising:
a handle, said handle comprising an outer surface, said handle further comprising a guide for determining the position of said outer surface of said handle, said guide comprising a first flattened surface portion of said outer surface, said first flattened surface portion of said outer surface being configured to slidingly engage the rim of the container and to resist rotation of said handle relative to the rim of the container, said first flattened surface portion facing in a first direction, and a second flattened surface portion of said outer surface, said second flattened surface portion facing in a second direction;
a terminal member, said terminal member comprising a first leg having an elongated dimension, and a second leg having an elongated dimension, said elongated dimension of said first leg being greater than said elongated dimension of said second leg, said first and second legs being connected to said handle;
a first tip connected to and angularly extending from said second leg;
a second tip connected to and angularly extending from said second leg; and
said first leg, second leg, first tip, and second tip forming a concave pocket.

13. The apparatus of claim 12 in which said handle further comprises a rounded intermediate portion lying between said first and second flattened surface portions of said outer surface of said handle.

14. The apparatus of claim 12 in which said first and second flattened surface portions of said handle comprise control surfaces for the fingers of a user during orientation of said handle by the user.

* * * * *